(12) United States Patent
Reynaud et al.

(10) Patent No.: US 11,054,370 B2
(45) Date of Patent: Jul. 6, 2021

(54) SCANNING DEVICES FOR ASCERTAINING ATTRIBUTES OF TANGIBLE OBJECTS

(71) Applicant: BRITESCAN, LLC, Petaluma, CA (US)

(72) Inventors: Danica T. H. Reynaud, Cotati, CA (US); Daniel D. Reynaud, Cotati, CA (US)

(73) Assignee: BRITESCAN, LLC, Petaluma, CA (US)

( * ) Notice: Subject to any disclaimer, the term of this patent is extended or adjusted under 35 U.S.C. 154(b) by 0 days.

(21) Appl. No.: 16/947,613

(22) Filed: Aug. 10, 2020

(65) Prior Publication Data
US 2020/0400586 A1 Dec. 24, 2020

Related U.S. Application Data

(63) Continuation-in-part of application No. 16/946,254, filed on Jun. 12, 2020, which is a continuation of
(Continued)

(51) Int. Cl.
*H04N 7/18* (2006.01)
*G01N 21/88* (2006.01)
(Continued)

(52) U.S. Cl.
CPC ..... *G01N 21/8851* (2013.01); *G01N 33/0098* (2013.01); *G06F 3/0488* (2013.01);
(Continued)

(58) Field of Classification Search
CPC ........... G01N 21/8851; G01N 33/0098; G01N 2021/8887; H04N 7/18; H04N 5/2253;
(Continued)

(56) References Cited

U.S. PATENT DOCUMENTS 5,313,373 A * 5/1994 Bjorner .................... B07C 3/14
362/17
8,040,502 B2 * 10/2011 Thomas ............... G01N 21/896
356/237.2
(Continued)

OTHER PUBLICATIONS

Brosnan T. et al. 2017. "Improving quality inspection of food products by computer vision—a review" Agric Rev, 38: 94-102.
(Continued)

*Primary Examiner* — Trang U Tran
(74) *Attorney, Agent, or Firm* — Perkins Coie LLP

(57) ABSTRACT

A scanning device that has a housing including an opaque wall configured to position an imaging device (e.g., still or video camera) to capture an image of a tangible object, a staging area (e.g., transparent wall, opening) opposite of the opaque wall, and an opaque body extending between the opaque wall and the staging area. The scanning device has a chamber that enables the imaging device to capture the image relative to the staging area. A focal distance from the imaging device to the staging area enables capturing a physical characteristic (e.g., a color, size, shape, texture, pattern) of the tangible object in the image at a resolution that enables ascertaining an attribute (e.g., authenticity, purity, or quality) of the tangible object. The opaque body can have an expandable structure to increases or decrease a focal distance to the tangible object.

25 Claims, 14 Drawing Sheets

Related U.S. Application Data application No. 16/534,847, filed on Aug. 7, 2019, now Pat. No. 10,684,231.

(60) Provisional application No. 62/715,736, filed on Aug. 7, 2018.

(51) Int. Cl.

| | |
|---|---|
| *G01N 33/00* | (2006.01) |
| *G06F 3/0488* | (2013.01) |
| *G06K 9/46* | (2006.01) |
| *H04N 5/232* | (2006.01) |
| *H04N 5/225* | (2006.01) |
| *G06K 9/60* | (2006.01) |
| *G06T 7/00* | (2017.01) |

(52) U.S. Cl.
CPC ............... *G06K 9/46* (2013.01); *G06K 9/60* (2013.01); *G06T 7/0002* (2013.01); *H04N 5/2253* (2013.01); *H04N 5/23216* (2013.01); *H04N 7/183* (2013.01); *G01N 2021/8887* (2013.01); *H04N 5/23222* (2013.01)

(58) Field of Classification Search
CPC .. H04N 5/23216; H04N 7/183; G06F 3/0488; G06K 9/46; G06K 9/60; G06T 7/0002
USPC .......................................................... 348/143
See application file for complete search history.

(56) References Cited

U.S. PATENT DOCUMENTS

| | | | | |
|---|---|---|---|---|
| 8,049,814 | B2 * | 11/2011 | Leibler | G03H 1/0005 348/360 |
| 9,857,664 | B1 * | 1/2018 | Tang | G03B 15/06 |
| 10,422,576 | B2 * | 9/2019 | Park | F25D 29/00 |
| 10,578,851 | B2 * | 3/2020 | Fletcher | G02B 21/0008 |
| 10,605,740 | B2 * | 3/2020 | Wolter | G01N 21/314 |
| 2017/0032285 | A1 | 2/2017 | Sharma et al. | |

OTHER PUBLICATIONS

Chopde S, et al. 2017. "Developments in computer vision system, focusing on its applications in quality inspection of fruits and vegetables—a review" Agric Rev, 38: 94-102.

Cubero S, et. al. 2011. "Advances in Machine Vision Applications for Automatic Inspection and Quality Evaluation of Fruits and Vegetables" Food Bioprocess Technol 4:487-504.

Krishna KP, et al. 2012. "Machine vision system: a tool for quality inspection of food and agricultural products" J Food Sci Technol 49(2):123-141.

Kumar N, et al.2012. "Leafsnap: a computer vision system for automatic plant species identification" Computer Vision—ECCV: 502-516.

Rateni G, et al. 2017. Smartphone-based food diagnostic technologies: a review. Sensors, 17: 1453.

Van Horn G, et. al. 2018. "The iNaturalist Species Classification and Detection Dataset" IEEE/CVF Conference on Computer Vision and Pattern Recognition Jun. 18-23, 2018. 10 pages.

Wäldchen J., et al. 2018. "Plant species identification using computer vision techniques: a systematic literature review" Arch Computat Methods Eng, 2025: 507-543.

AgShift, "AgShift—Harness Data. Harvest Profits." Retrieved online at http://www.agshift.com/ Aug. 8, 2019. 1 page.

Bext360, "Best360—Every. Single. Step." Retrieved online at http://www.bext360.com/ Aug. 8, 2019. 2 pages.

Consumer Physics, "SCiO—The World's First Pocket Sized Molecular Sensor" Retrieved online at https://www.consumerphysics.com/ Aug. 8, 2019. 1 page.

Dillenberger, D. "Pairing AI with Optical Scanning for Real-World Product Authentication" May 23, 2018. Retrieved online at https://www.ibm.com/blogs/research/2018/05/ai-authentication-verifier/ Aug. 8, 2019. 5 pages.

IBM, "5 in 5: Crypto anchors and blockchain" Retrieved online at https://www.research.ibm.com/5-in-5/crypto-anchors-and-blockchain/ Aug. 8, 2019. 10 pages.

Nima, "Nima—A Portable Gluten Tester" Retrieved online at https://www.nimasensor.com/ Aug. 8, 2019. 9 pages.

Tellspec, "Food Analysis, Food Safety, Food Database, Food Security" Retrieved online at http://tellspec.com/eng/. 2 pages.

\* cited by examiner

SCANNING DEVICES FOR ASCERTAINING ATTRIBUTES OF TANGIBLE OBJECTS

CROSS-REFERENCE TO RELATED APPLICATIONS

This application is a continuation-in-part of U.S. patent application Ser. No. 16/946,254, filed Jun. 12, 2020 and titled "PORTABLE SCANNING DEVICE FOR ASCERTAINING ATTRIBUTES OF SAMPLE MATERIALS," which is a continuation of U.S. Pat. No. 10,684,231, filed Aug. 7, 2019 and titled "PORTABLE SCANNING DEVICE FOR ASCERTAINING ATTRIBUTES OF SAMPLE MATERIALS," which claims priority to U.S. provisional patent application Ser. No. 62/715,736, filed on Aug. 7, 2018 and titled "TECHNOLOGY FOR ASCERTAINING THE QUALITY AND AUTHENTICITY OF PLANT MATERIALS," which are incorporated herein in their entireties by this reference.

TECHNICAL FIELD

The disclosed teachings generally relate to a scanning device, and more particularly relate to a scanning device configured to ascertain attributes of a tangible object.

BACKGROUND

Global supply chains include tangible objects sourced and distributed throughout the world. Due to the reach of global supply chains, the sources of the tangible objects may not be authenticated by a trusted source. For example, biological materials are sourced and used throughout developed and developing countries for consumption, as home remedies, and in drug products. Examples include plant materials such as herbs (e.g., parsley) and spices (e.g., cinnamon) and animal materials such as meat and fish. Non-biological objects such as cosmetics, documents, money, and machine parts are likewise part of global supply chains. Accordingly, there is a large and distributed global market for tangible objects. The tangible objects can be pre-processed at their sources before distribution to suppliers, manufacturers, retailers, or consumers. For example, plant and animal material may be fresh, dried, cooked, whole, chopped, minced, or ground.

Characteristics such as the color, size, shape, texture, or pattern of biological materials may vary depending on the genetics of the individual species and the natural conditions when and where the plant material is grown or animal is raised. Examples include the geographic region for cultivation, soil composition, water quality, weather conditions including temperature and humidity, sunshine intensity, and growth period. In another example, tangible objects may be contaminated with hazardous impurities such as animal fecal matter, contaminants such as rocks and sticks, or adulterated with fillers such as rice or soy powder. The attributes of money, documents, and other non-biological objects have also become more important as the sources of those tangible objects become more diverse and supply chains are decentralized with fewer centralized controls.

As a result, intermediaries in distribution chains of commerce seek to ascertain attributes (e.g., authenticity, purity, quality) of tangible objects. In conventional techniques, the attributes of tangible objects can be subjectively judged based on a skilled person's experience by observing the shape and color of a sample, or in smelling flavor and/or via chewing materials. As a result, conventional techniques are unreliable and inconsistent because people are not uniformly trained to evaluate diverse tangible objects. Moreover, smaller or foreign sources are not usually subjected to validation by a trusted third-party that can vouch for the attributes of tangible objects from those sources.

Existing systems or devices that can provide reliable and consistent information regarding the attributes of tangible objects involve complex and cost-prohibitive machinery operated by highly-skilled technicians. For example, systems or devices that can reliably test quality and authenticity at the chemical or genetic level to determine purity and contaminants are implemented in a few scientific laboratories or at sophisticated manufacturing facilities. Diagnostic testing systems use expensive optical sensors and equipment (e.g. FTIR and NIR spectrophotometers), require adherence of costly and destructive optical signatures to materials, and require technical experts to develop databases and to operate the systems. As a result, reliable, affordable, and flexible techniques are unavailable to laypeople. Consequently, for example, tangible objects sourced in large and small countries throughout the world and shipped to the U.S. may not have been reliably tested for attributes due to a lack of affordable and flexible methods. Accordingly, a need exists for cost-effective and scalable techniques for ascertaining attributes of tangible objects, without highly trained experts or cost-prohibitive equipment.

SUMMARY

The disclosed embodiments include a scanning device that has a housing including an opaque wall configured to position an imaging device (e.g., still or video camera) to capture an image of a tangible object, a staging area (e.g., transparent wall, opening) opposite of the opaque wall, and an opaque body extending between the opaque wall and the staging area. The scanning device has a chamber that enables the imaging device to capture the image relative to the staging area. A focal distance from the imaging device to the staging area enables capturing a physical characteristic (e.g., a color, size, shape, texture, or pattern) of the tangible object in the image at a resolution that enables ascertaining an attribute (e.g., authenticity, purity, or quality) of the tangible object.

The opaque body can have an expandable structure that increases the focal distance by extending the expandable structure and decreases the focal distance by retracting the expandable structure. In some embodiments, the expandable structure includes accordion-like baffles to change a length or width of the opaque body.

The imaging device can be integrated into the scanning device or included in a handheld mobile device that is disposed on an exterior surface of the opaque wall with the imaging device facing inside the chamber through an opening on the opaque wall.

When the staging area includes an opening to an exterior environment, the distance from the imaging device to an exterior staging surface on which the tangible object is disposed can be greater than the length of the opaque body such that an external environmental light illuminates the tangible object. The staging surface is separate from the scanning device. Examples of a staging surface include a table, floor, human tissue, etc.

When the staging area includes a transparent wall, the scanning device can include a light source that illuminates a staging area through the transparent wall, where the tangible object is disposed on the staging surface. The transparent wall can be removable and include a light filter such that the captured image is filtered by the light filter. The scanning device can create a controlled environment that blocks out external light when the transparent wall is sealed against the staging surface and the tangible object is disposed between the transparent wall and the staging surface.

In some embodiments, the scanning device includes computing resources to detect the physical characteristic in the image and determine the attribute of the tangible object based on the detected physical characteristic processed through a machine learning (ML) model that is trained based on a dataset of physical characteristics and attributes. The scanning device can include or use a biometric sensor or software to perform authentication of the user, either through an integrated fingerprint recognition device (or on a touchscreen), or via voice or facial recognition. The authenticity of the user is a data point that is not a physical characteristic of the sample tangible object, but which can be used to infer an attribute of the tangible object. For example, the authenticity of the user can be used as a proxy for the authenticity of the tangible object captured in a photograph.

In some embodiments, the scanning device can use the computing resources of a mounted handheld mobile device to communicate, over a wireless network, image data of the image to a server computer, where a physical characteristic is detected at the server computer, and then receive an indication of an attribute of the tangible object.

This Summary is provided to introduce a selection of concepts in a simplified form that are further explained in the Detailed Description. This Summary is not intended to identify key features or essential features of the claimed subject matter, nor is it intended to be used to limit the scope of the claimed subject matter.

DETAILED DESCRIPTION

Figure 1A:
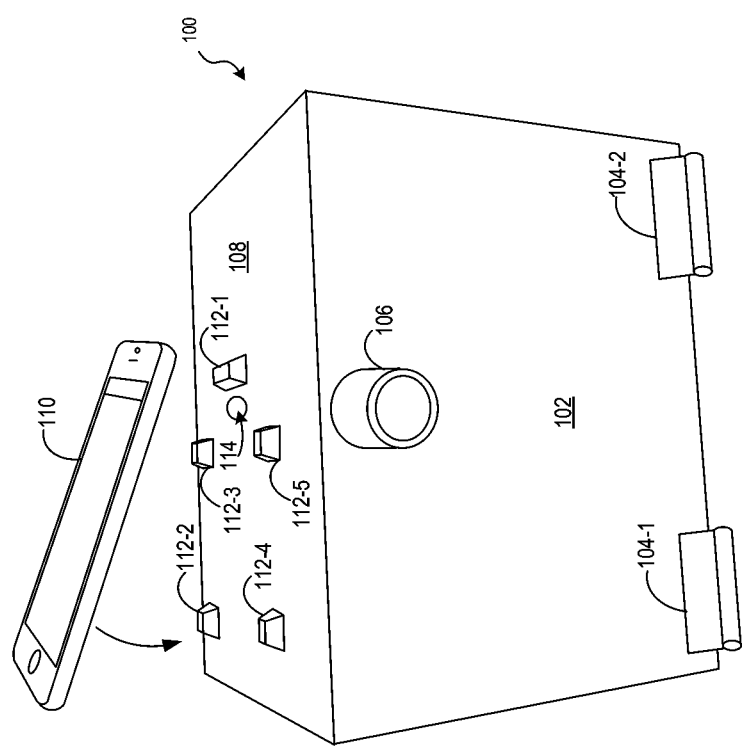
FIG. 1A illustrates a scanning device in a closed-door configuration that can capture images of a tangible object contained therein.

The embodiments set forth below represent the necessary information to enable those skilled in the art to practice the embodiments and illustrate the best mode of practicing the embodiments. Upon reading the following description in light of the accompanying figures, those skilled in the art will understand the concepts of the disclosure and will recognize applications of these concepts that are not particularly addressed here. It should be understood that these concepts and applications fall within the scope of the disclosure and the accompanying claims.

The purpose of terminology used herein is only for describing embodiments and is not intended to limit the scope of the disclosure. Where context permits, words using the singular or plural form may also include the plural or singular form, respectively.

As used herein, unless specifically stated otherwise, terms such as "processing," "computing," "calculating," "determining," "displaying," "generating," or the like, refer to actions and processes of a computer or similar electronic computing device that manipulates and transforms data represented as physical (electronic) quantities within the computer's memory or registers into other data similarly represented as physical quantities within the computer's memory, registers, or other such storage medium, transmission, or display devices.

As used herein, terms such as "connected," "coupled," or the like, refer to any connection or coupling, either direct or indirect, between two or more elements. The coupling or connection between the elements can be physical, logical, or a combination thereof.

The modern world is filled with tangible objects that people obtain from various sources including global supply chains and local sources. Tangible objects can be natural or manmade, organic or non-organic, and in different states (e.g., solid, liquid, gel). Tangible objects can include, or be included in, processed material in various forms such as pieces, granules, powder, etc. A common feature of tangible objects is that they have one or more physical characteristics (e.g., properties) that are perceptible by human senses. Examples of physical characteristics include color, size, shape, texture, or pattern of one or more tangible objects. Further, a tangible object can have different physical characteristics at different points in time of the object's lifecycle. For example, an object such as a gem can become worn and dull overtime.

A tangible object is oftentimes the end-product of pre-processing at different points (e.g., locations) of a supply chain. For example, various materials (e.g., plant material) that are sourced and used throughout developed and developing countries are typically pre-processed (e.g., dried, chopped, ground) before being traded in commerce. The processing can inadvertently mix in undesired materials or substances that contaminate a product. Given the variety of tangible objects sourced throughout the world and the complexity of supply chains, ascertaining attributes of a tangible object is exceedingly important. Examples of the attributes include an authenticity, purity, and quality of a tangible object.

Examples of tangible objects include edible and non-edible objects. Edible objects include foods, supplements, herbs and spices, fish, meat, seafood, vitamins, beverages, oils, other liquids (e.g., vinegar), and edible ingredients put into foods, etc. Examples of non-edible objects include cosmetics, essential oils, soils, chemicals, minerals, jewelry, metals, textiles, paper, paint, ink, gems, plants (e.g., poisonous), animals (e.g., pests), filth (e.g., pests, rocks, twigs, animal excrement), collectibles (e.g., trading, cards), fungus/molds, certificates or documents, signatures, money, government issued identification cards, human/medical features (e.g., skin, hair, urine, blood, stool), pharmaceuticals/drugs, machined parts (e.g., screws), fingerprints, etc.

Ascertaining one or more attributes of tangible objects from diverse sources and with diverse properties is important to maintaining the integrity of supply chains and products, as well as establishing the trustworthiness of their sources. The attributes of interest to entities can depend on types of tangible objects. For example, a quality attribute can include the freshness, density, homogeneity, levels of chemicals, or aroma of a tangible object. An authenticity attribute can include identifying a species or determining whether an alleged source of a tangible object is the actual source of the tangible good (e.g., distinguishing between fake and authentic trading cards, certificates, or documents seals). A purity attribute can include detecting the presence of adulterants, contaminants, substitutes, filth, dyes, or fillers in tangible products. Another example is a provenance attribute to determine the origin of a tangible object (e.g., the providence of agriculture). Other examples of attributes include a size, color, number/quantity, condition, extent of diseased or damaged tissue, or any other feature of a tangible object that can be derived from physical characteristics of that tangible object.

The ability to ascertain the attributes of tangible objects can be incorporated into various existing processes to validate the integrity of those processes. For example, distributors seek to check that component parts of a tangible object are unadulterated at points of geographically distributed manufacturing or supply chains. This includes the ability to track component parts through a supply chain. In yet another example, a patient or healthcare professional may seek to identify the state of diseases tissue, check a condition, or determine the level or extent of damaged or irregular tissue (e.g., determine the state of an irregular mole on a person's skin). In yet another example, law enforcement or detectives may seek to identify a person based on a print of a fingerprint on a tangible object.

A conventional technique for ascertaining attributes of tangible objects include manual assessments by highly trained professionals or technicians. For example, a gemologist is trained to ascertain the attributes of natural or artificial gemstones, a dermatologist is trained to ascertain the attributes of a skin condition, a botanist is trained to ascertain attributes of plants, a metallurgist is trained to ascertain the attributes of metals, etc. The reliance on trained persons to ascertain attributes of tangible objects is problematic for various reasons. First, there are few highly trained professionals relative to sources of tangible objects. Accordingly, using highly trained professionals is cost-prohibitive and impractical. As a result, consumers must pay more for products to ascertain attributes of tangible objects or pay less and accept the risk of not knowing the attributes of products. Second, the attributes can be unreliable and inconsistent because different people assess tangible objects in different ways due to different trainings or bias.

A solution to using cost-prohibitive professionals includes complex machinery, scientific equipment, or sophisticated techniques that involve advanced technologies such as optics, chemical reactions, genetic analysis, and other forms of analytics that can provide consistent outcomes. However, sophisticated technology and techniques are also cost-prohibitive and are accessible to only a small fraction of commercial markets. That is, individual manufacturers, distributors, or consumers lack access to reliable ways to determine attributes of tangible objects with consistent results.

The disclosed technology overcomes the aforementioned drawbacks with a standalone or distributed system that includes a relatively inexpensive scanning device. As such, numerous scanning devices can be distributed across entire commercial markets to uniformly ascertain attributes of widely distributed tangible objects. The scanning device has a minimum number of components (e.g., mechanical, electronic, optical) to frame or stage samples of tangible objects for capturing images (e.g., pictures) consistently. The scanning device is not limited to ascertaining attributes of tangible objects in an enclosed chamber. Instead, the scanning device can enable analyzing anything that fits within a frame defined by a chamber and that has at least one physical characteristic (e.g., color, size, shape, texture, pattern) that can be captured by an imaging device. The device can determine the attribute of a tangible object that can be detectable or undetectable by an unaided human eye. The scanning device can analyze the tangible objects (e.g., biological and/or non-biological materials such as finished foods and supplements and their ingredients, meats, fish, seafood, oils, beverages, cosmetics, gems, soil) of various sizes, in various locations, and by people without specialized training.

In some embodiments, a handheld mobile device (e.g., mobile phone) is mounted on the scanning device to capture digital pictures of a sample contained within the scanning device. The mobile phone can be communicatively coupled to an attribute determination service ("service") over a cellular or computer network. The disclosed embodiments can take advantage of the ubiquity of mobile phones in developed and developing countries to enable a process for reliably ascertaining the attributes of tangible objects in a cost-effective manner. The backend service can be centralized or distributed to collect images of various tangible objects. The images can be processed with an artificial intelligence system of a service to determine the attributes of tangible objects.

In some embodiments, a mobile application of the service allows users to ascertain the attributes of tangible objects in commerce by using smartphones. The image data of images captured by a smartphone or another imaging device can be uploaded into a network portal on either the smartphone or a personal computer. To ensure consistency in image quality, some embodiments of the scanning device are designed for using a variety of mobile phones to capture images of tangible objects that can be processed by machine learning (ML) algorithms and compare against training data sets and analyze the image data for attributes. That is, a variety of mobile phones can be calibrated to use the scanning device.

In some embodiments, image data is transferred via a computing interface (e.g., an application programming interface (API)) to a computing system (e.g., cloud-based, local hosting, offline computing) that implements image recognition and analysis software programs, which can use computer vision (CV)/ML or other similar algorithms to detect and classify features of the image data. Images that are collected to develop a database for ascertaining the attributes of tangible objects (e.g., training set for an ML model) can be obtained with smartphones or other types of imaging devices mounted on scanning devices to capture images of samples of tangible objects that have been independently verified via any number of known methods (e.g., morphology, chemistry, and/or DNA sequencing). The image recognition and analysis algorithms can be executed locally at the scanning device or the mobile device, and train the ML model locally based on the locally captured images.

The results that are output by the service can be returned through a computing interface to a local user interface of the handheld mobile device or computer of the scanning device. In some embodiments, a user can view resulting statistics and trends, and generate and share certificates of analyses. In some embodiments, the images, sample information, and results are returned through a computing interface to external software (e.g. supply-chain management or blockchain for persistent storage). For example, image data captured by the scanning device can be stored in a blockchain to track a tangible object through a supply chain. Thus, the disclosed embodiments include applications for authenticating plant and animal species, detecting adulteration and filth, assessing quality and manufacturing specifications, and tracking specific lots or samples through a supply chain. Further, the disclosed embodiments can be validated so that product suppliers and manufacturers can use it to comply with internal quality control specifications or other governmental regulations, such as the US Food and Drug Administration's current Good Manufacturing Practices.

The embodiments are the first known application of its kind designed for authentication and quality control evaluation of tangible objects (e.g., plant materials) in commercially traded forms (e.g., processed) such as dried, chopped, and powdered herbs or spices. In the context of plants, examples of existing technologies for identification include PLANTSNAP, LIKETHATGARDEN, LEAFSNAP, FLOWERCHECKER, PLANTIFIER, NATUREGATE, AND IPFLANZEN. These technologies are designed to identify species based on a whole living plant, leaves, or flowers, not the commercially traded forms of plant materials. The images used to generate the reference databases are usually not verified by independent experts, or they are extracted from GOOGLE IMAGE searches. In contrast, the disclosed embodiments can use verified samples for reference images contained in the database. Moreover, the disclosed embodiments uniquely provide a scanning device to ensure that the reference and test image data is uniform. This allows the disclosed technology to detect subtle differences between samples that are not possible without taking images in a controlled environment, including controlled lighting, background color, sample placement, and focal distances.

Some embodiments include a scanning device that is portable, inexpensive, and designed for ascertaining attributes of different types of tangible objects. In particular, embodiments include a small and lightweight box composed of durable white, opaque, PVC, or similar materials. The scanning device and associated trays have several advantageous features. For example, embodiments of the scanning device can eliminate external light, provide consistent internal lighting, consistent focal distance and background color, provide for consistent amounts of a tangible object, and ensure that samples are in the same position in a captured image so that software can consistently crop or analyze a specific area or areas of the captured image. The distance from a staging surface that stages the sample to the optical component of the handheld mobile device can be adjustable to have the closest focal distance, to take clear high-quality images by using most any smartphones. Moreover, a lower staging surface can allow for capturing images of larger-sized materials. In some instances, the staging surface has a marker (e.g., a logo) printed on its surface to enable the imaging device to complete an autofocus process and for calibration. In some embodiments, a marker can indicate where the sample should be placed and could include a dot, a printed shape, raised sides, or a depression. The marker can be essential for analyzing powdered, light-colored, relatively small, or highly-processed materials because a camera cannot readily autofocus on these materials.

An embodiment includes a five-sided box with a hinged door on the top, bottom, or side edge of the box. The box can have an approximate size of 200 mm (length)×150 (width)×125 (height). An internal chamber of the box can have removable lights (e.g., white, colored, incandescent, LED, ultraviolet (UV) or infrared (IR) light that are battery-powered and independently operable. A smartphone can be placed on the top of the box with its camera lens positioned over a one-inch hole into the chamber. The box can have four legs, which are unnecessary if a knob or pull is not required to open the door. For example, the box can have a mechanism to press and release the door, or an indent, notch or handle on the side to open it. The chamber can hold shelf(s) for tray(s) that have compartments of different sizes and shapes for different tangible objects. For example, whole objects or less-processed materials go on a larger compartment of a tray, small objects can sit on smaller compartments, and liquids or powders can be held in a small square compartment of a tray offset from the center. The camera lens can face directly inside the box to capture images by switching the smartphone to camera mode. The box does not require a special lens, interface, or optical device attached to the camera. Lastly, the image data can be uploaded to a image analysis software through a web browser or native app on the smartphone for processing.

Figure 1B:
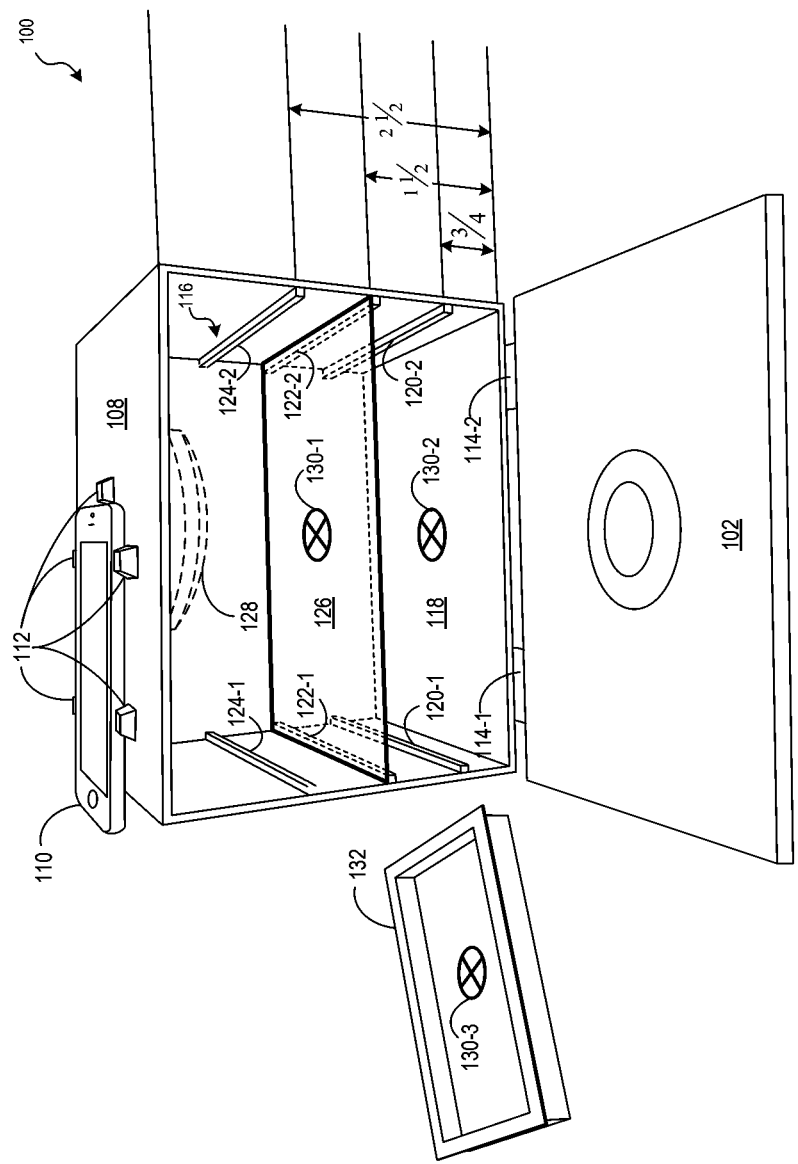
FIG. 1B illustrates the scanning device of FIG. 1A in an opened-door configuration.
Figure 1C:
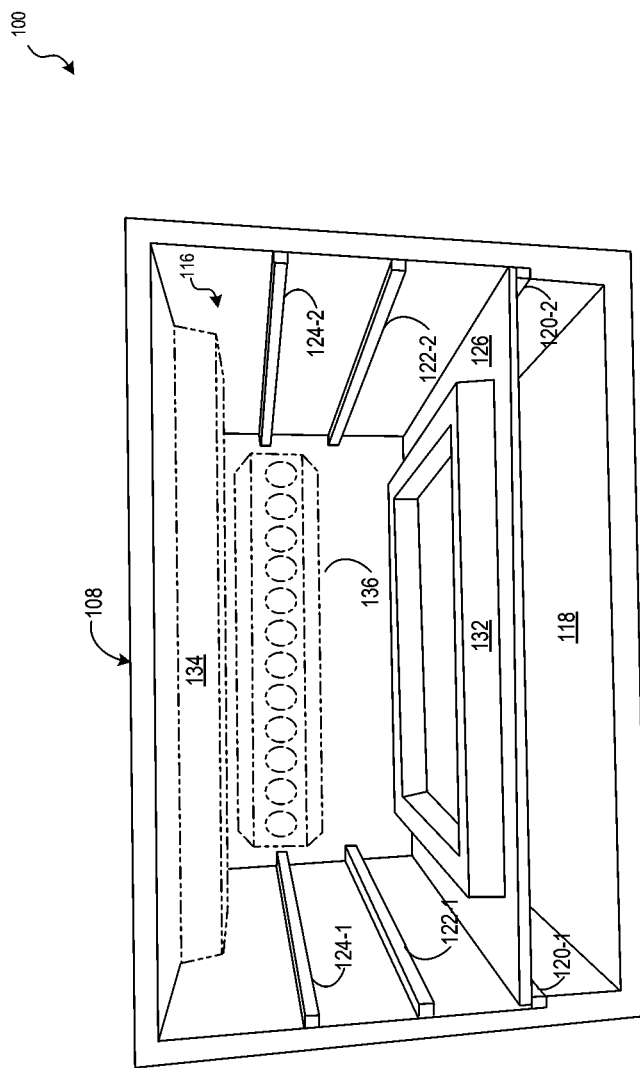
FIG. 1C illustrates a chamber of the scanning device of FIG. 1A.

For example, FIGS. 1A through 1C illustrate an embodiment of a scanning device 100. FIG. 1A illustrates the scanning device 100 in a closed-door configuration. As illustrated, the scanning device is a small, portable, and lightweight box that measures about 6"×6"×8". The scanning device 100 has an internal chamber (not shown) that functions as a controlled environment for capturing images of samples. The scanning device 100 includes an openable member 102 (e.g., a door) that enables access to the chamber. In some embodiments, an openable member can open like a door on a side hinge(s), roll up/sideways/down, or be made of a flexible material (i.e. a curtain) that can be either pushed up/sideways/down.

A staging surface such as a shelf (not shown) inside the chamber can receive a tray with a tangible object. As illustrated, the openable member 102 is attached to scanning device 100 with hinges 104-1 and 104-2, and a handle 106 is used to open the openable member 102. The ambient light of an external environment is blocked from the chamber when the openable member is sealed closed. An exterior surface 108 of the scanning device 100 receives a handheld mobile device 110, which includes an imaging device (e.g., camera device). The handheld mobile device 110 is secured to the exterior surface 108 with one or more positioners 112-1 through 112-5 that are shaped like bumps. An opening 114 through the exterior surface 108 to the chamber enables the handheld mobile device 110 to capture images of sample material when its camera lens is positioned over the opening 114. The scanning device 100 can include a mechanism to open or close any number of holes on different exterior surfaces of the scanning device 100 to accommodate multiple mounted devices (e.g., smartphones) to capture any number of images at the same time or to capture images from different angles.

FIG. 1B illustrates the scanning device 100 in an opened-door configuration. The chamber 116 can define level(s) for shelf(s) at predefined distances from the opening 114 (not shown) through the exterior surface 108. The shelf(s) are adjustable to change a focal distance to the camera. The floor 118 of the chamber 116 is furthest from the opening 114. The chamber 116 has support structures 120-1, 120-2, 122-1, 122-2, 124-1, and 124-2 that can support a removable shelf 126. For example, the level formed by the support structures 120-1 and 120-2 can support the shelf 126 at a predefined distance to the opening 114. Another level formed by the support structures 122-1 and 122-2 support the shelf 126 at another predefined distance, closer to the opening 114 compared to the level formed by the support structures 120-1 and 120-2. The support structures 124-1 and 124-2 can support the shelf 126 at a closest predefined distance to the opening 114 compared to the other predefined distances.

In some embodiments, the scanning device has fixed staging surfaces (e.g., shelves) that are not removable at different focal distances from the imaging device. Various samples can be disposed on the fixed shelves (including the bottom of the chamber). The fixed shelves can span an area less than the entire diameter of the scanning device so that an imaging device can capture an image that includes samples at the different focal distances from the imaging device.

The scanning device 100 can use a light source of the handheld mobile device 110 to illuminate the sample material in the chamber 116. For example, the opening may be sufficiently large to allow light from a source of the handheld mobile device 110 to illuminate the sample material in the chamber 116. In some embodiments, the scanning device 100 includes a light source 128 that can radiate light on the sample material when disposed on the shelf 126. Examples of the light generated by the light source 128 includes incandescent, LED, white, colored, UV, or IR light. As shown, the light source 128 is positioned on the ceiling of the chamber 116, has a circular shape, is removable, and faces the floor 118 (e.g., bottom or lowest wall) of the chamber 116. The camera device of the handheld mobile device 110 faces the shelf 126 such that the light source 128 illuminates an area including the field-of-view of the camera.

FIG. 1C illustrates the chamber 116 with a combination of two or more removable light sources. For example, the light sources can be attached to the surfaces of the chamber 116 or inside a surface of the door (not shown) by using magnets. As shown, the down-facing light source 134 is positioned on the ceiling of the chamber 116, has an elongated shape, is removable, and faces the floor 118 of the chamber 116. The forward-facing light source 136 is positioned on the rear wall of the chamber 116, has a rectangular shape, is removable and faces the door (not shown) of the scanning device 100. Further, the forward-facing light source 136 is positioned to provide different amounts of light depending on the level at which the sample is located. For example, the forward-facing light source 136 radiates more light at the level furthest from the floor 118 (closest to the opening 114 (not shown).

The shelf 126 includes a marker 130 that enables the camera of the handheld mobile device 110 to autofocus on the shelf 126 relative to the marker 130. The floor 118 also includes a marker 130-2 that enables the camera of the handheld mobile device 110 to autofocus on the floor 118. The scanning device 100 can contain any number of cameras inside the chamber, either on one surface or multiple surfaces (e.g., top, bottom, side views). The optional removable trays of the scanning device 100 can hold samples of tangible objects, and the tray is placed on the shelf 126. For example, the main tray 132 can include a marker 130-3 that enables the camera of the handheld mobile device 110 to autofocus on the surface of the main tray 132. The scanning device 100 can utilize trays of different shapes and sizes that facilitate ascertaining attributes of different samples. The trays are washable, reusable, and can have a matte surface to reduce reflection. In most cases, the trays are white but could be black or other colors.

In one example, the main tray 132 can hold about 60 ml (¼ cup) of processed material across about a 4" by 5" area, hold a single object, or hold multiple small objects. The removable trays may be bigger/smaller trays relative to the shape and design of a chamber. As shown, the main tray has a raised lip around a rectangle in the center that holds the sample material. The area is optimized so that the imaging device of the handheld mobile device 110 can capture an image of the entire area without having to crop the edges of the captured image. Hence, the entire image can be analyzed to ascertain an attribute of the sample material.

Figure 4:
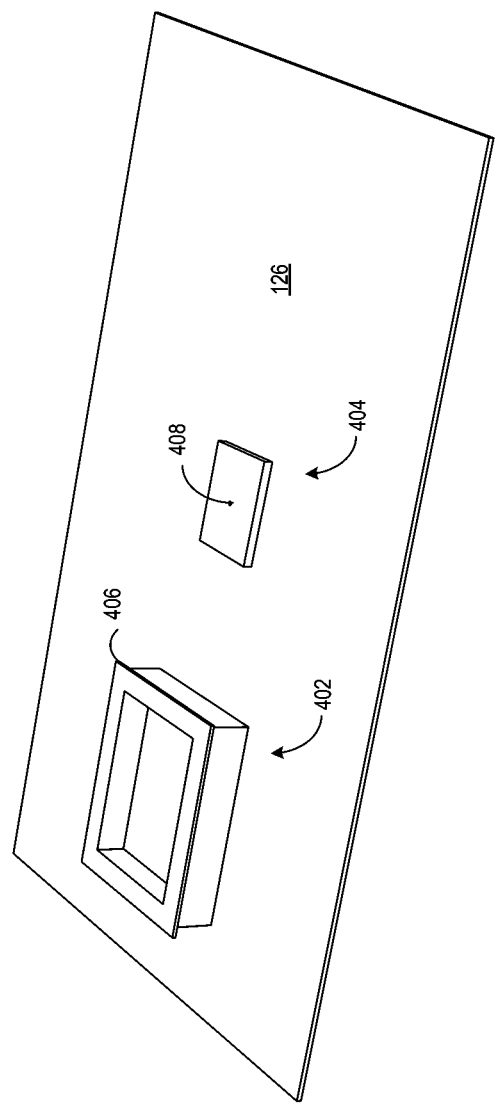
FIG. 4 illustrates a shelf with different trays thereon for tangible objects.

FIG. 4 illustrates an example of a shelf with specialty trays that can hold different forms or amounts of a tangible object. The specialty tray 402 is a small rectangle in the center or offset to hold smaller amounts of materials. This design can be optimized for 10 ml (2 teaspoons) of powder material or liquid and fit standard disposable weigh boats. The specialty tray 402 has a raised lip around the edges to put material on the tray. The specialty tray 404 is a flat square and/or has small dot on the center to hold a relatively small object. The square for liquids is placed in an area on the tray to avoid light reflection or shadows from the hole on top. In some embodiments, a tray for the scanning device has different sampling areas to hold different types or amounts of a tangible object thereby obviating the need for specialty trays for different types of tangible objects. An image of different tangible objects can be captured simultaneously, segmented from each other by the imaging processing software, and separately analyzed to detect an attribute for each tangible object. As such, a chamber of a scanning device can be configured to hold multiple samples of tangible objects to capture a single image of all of them and analyze the samples together or separately.

The image processing software of the service can crop out areas of the tray that were captured in an image of the tangible object. In particular, the imaging device coupled to a scanner could capture images that include a tangible object alone or the tangible object and the stage on which the tangible object is placed, depending on the focal distance from the imaging device to the stage (e.g., shelf). For example, a tangible object on the tray 126 positioned on a topmost shelf (e.g., 124-1 and 124-2) of the chamber 116 has a shorter distance compared to positioning the tray 126 on the floor 118. An image of the tangible object captured when positioned on the topmost shelf would include less of the tray 126 compared to an image captured when the tray 126 is positioned on the floor 118. Rather than needing to adjust the zoom function of the imaging device, the image processing software can automatically detect the background as the tray 126's surface and automatically crop the image to only include the tangible object, where desirable. The background surface can be detected based on the color of the surface and/or markers on the surface.

Therefore, the four different level positions of the chamber 116 can hold the tray, depending on the size of the tangible object and desired focal length from the camera. Once the tangible object is placed at a level and the light source 128 is switched on, the openable member 102 is closed to seal the chamber from external light. The opening 114 on the top of the scanning device 100 then allows the camera to capture an image of the inside of the chamber 116 that contains the sample. In some embodiments, another lens, such as a magnifying or microscopic lens is attached or within the focal range of the camera lens of the imaging device to augment the function of the imaging device. For example, the chamber 116 can include multiple imaging devices, optical filters, or lenses, disposed between the imaging device and the tangible object to filter wavelengths for a captured image. These optical elements can be built into the scanning device, are removable, and/or exchangeable with other optical elements.

The scanning device is not limited to the embodiments illustrated in FIGS. 1A through 1C. For example, a scanning device can have a carrying handle that folds in/out. The positioners 112 on the top of the scanning device can be adjustable to position different types of handheld mobile devices (e.g., smartphones, tablet computers). In some embodiments, one or more of the positioners 112 are removeable or are omitted altogether. The scanner device can have integrated lights that run off a removable battery pack or plug into a wall outlet. In some embodiments, the scanning device has an integrated, rechargeable battery pack, an on/off switch/button, a hinged door or pull-out compartment, etc. The light sources can include combinations of white or colored LED or incandescent lights, UV or IR lights. Moreover, an internal light source may be triggered to automatically illuminate the chamber 116 only when the door is closed, and/or the tray is inserted. In some embodiments, rather than having small legs, the scanning device has a larger base with a pull mechanism for an openable member.

Figure 2A:
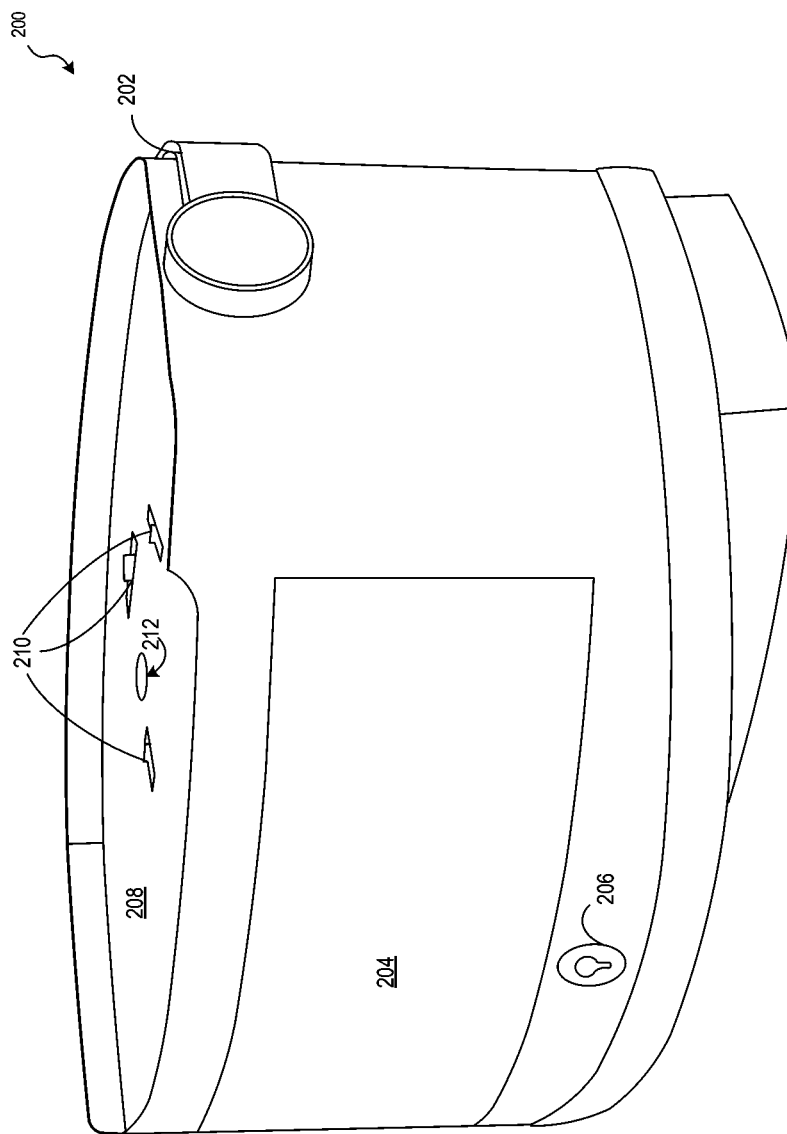
FIG. 2A illustrates a perspective view of another embodiment of a scanning device in a closed-door configuration.
Figure 2B:
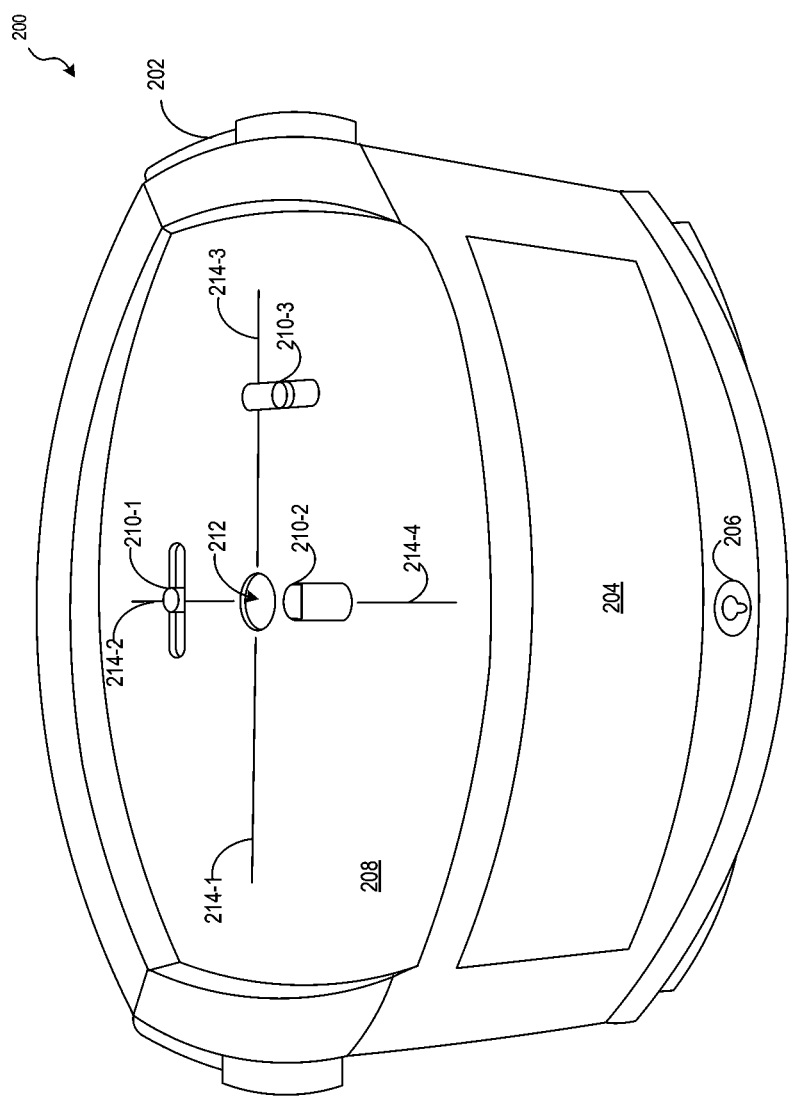
FIG. 2B illustrates a top-down view of the scanning device of FIG. 2A.
Figure 2C:
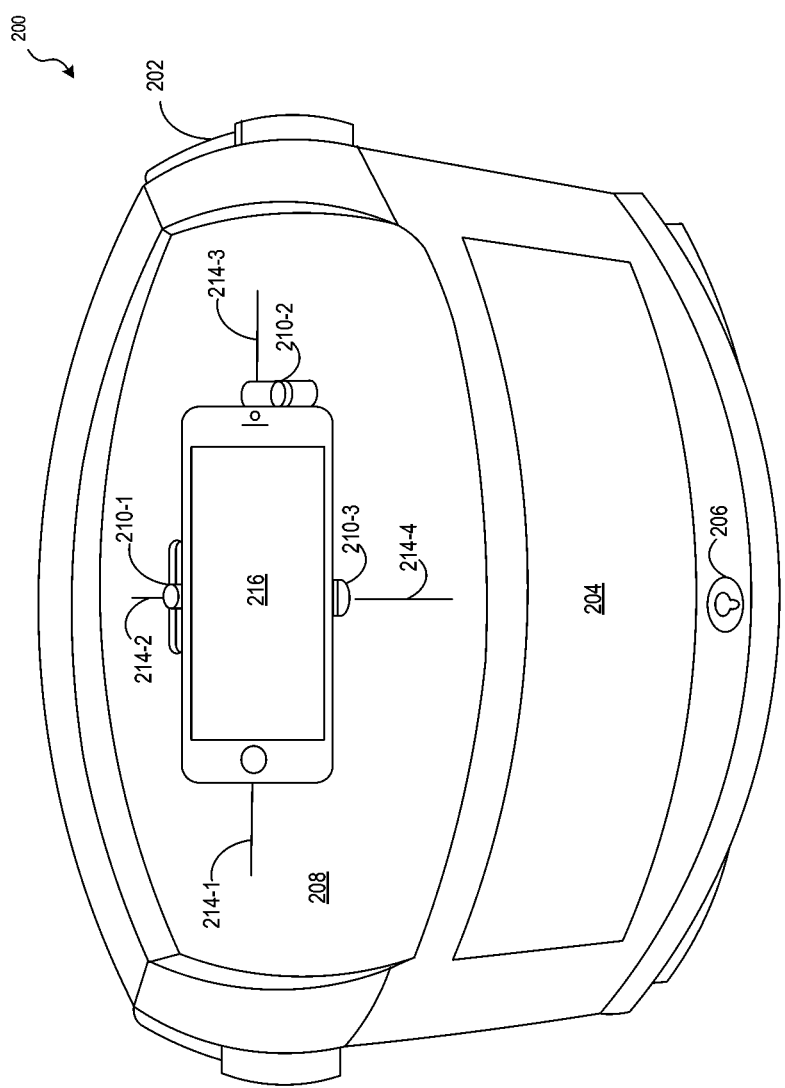
FIG. 2C illustrates the scanning device of FIG. 2A in a closed-door configuration with a handheld mobile device mounted thereon to capture images of a tangible object contained in a chamber of the scanning device.

FIGS. 2A through 2C illustrate another embodiment of a scanning device 200. Specifically, FIG. 2A illustrates a perspective view of the scanning device 200 with rounded edges in a closed-door configuration and FIG. 2B illustrates a top-down view of the scanning device 200. The scanning device 200 is portable and has a handle 202 for a user to carry the scanning device 200. The scanning device 200 has a chamber (not shown) that provides a controlled environment for capturing images of sample materials contained in the chamber. A push/pull openable member 204 allows a user to access the chamber. Similar to the previously described embodiments, a sample is placed on a tray that is placed on a removable shelf inside the chamber. As illustrated, a user can push a button 206 to open/close the openable member 204 to place/remove a sample. The light of an external environment is blocked from the chamber when the openable member 204 is closed.

An exterior surface 208 of the scanning device 200 can receive a handheld mobile device that includes a camera. The handheld mobile device is secured to the exterior surface 208 with one or more adjustable positioners 210-1 through 210-3. The positioners 210 are optional features that, in some embodiments, are unnecessary. For example, surface 218 can include markers to guide the user for positioning the handheld mobile device. An opening 212 through the exterior surface 208 to the chamber enables the camera of the handheld mobile device to capture the image of the sample material in the chamber.

FIG. 2B also shows markers 214-1 through 214-4 that aid the user in positioning a handheld mobile device so that its camera is over the opening 212. FIG. 2C illustrates the scanning device 200 in a closed-door configuration with the handheld mobile device 216 mounted on the exterior surface 208 to capture an image of a tangible object contained in the chamber. As shown, the handheld mobile device 216 is positioned on the exterior surface 208 such that the camera of the handheld mobile device 216 is positioned over the opening and faces the shelf in the chamber.

In another embodiment, an imaging device is built into a scanning device to capture images of samples without needing a separate handheld mobile device. The scanning device can also have a built-in interface such as a touchscreen on a top surface where the handheld mobile device normally sits. The scanning device itself may have a wireless interface to connect to Wi-Fi, cell service, and/or can connect to a handheld mobile device via, for example, BLUETOOTH. The scanning device can have a screen that allows a user to see sample material inside the chamber and allow the user to control when to capture images and send image data to a handheld mobile device or upload to a remote computer system.

The scanning device can also capture images using the built-in camera and store the images in a local memory. The scanning device can then upload the locally stored images to the system when the scanning device establishes a connection with the system. For example, the built-in camera can be controlled by the handheld mobile device to establish a connection with the system when available. The scanning device can also identify a tray and/or type of material in the chamber to automatically select a correct cropping or image processing function.

Figure 3:
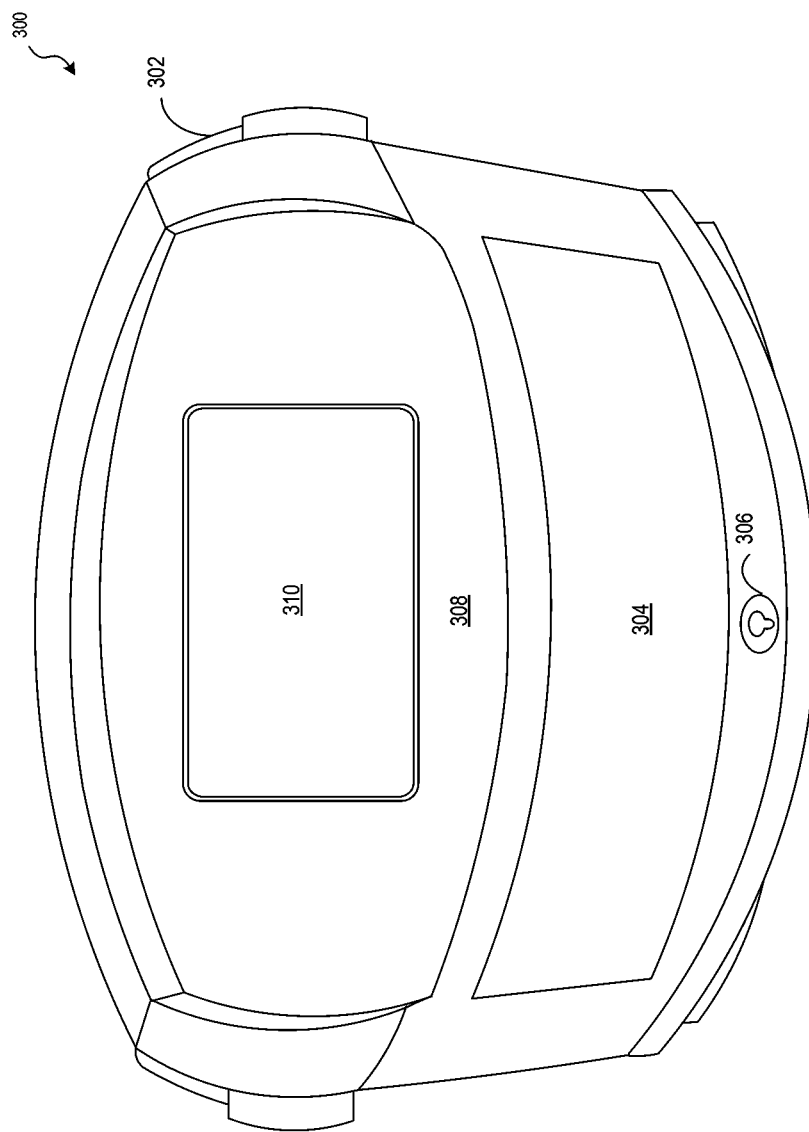
FIG. 3 illustrates another embodiment of a scanning device in a closed-door configuration with a built-in touchscreen to control a built-in camera to capture images of a tangible object contained in a chamber of the scanning device.

FIG. 3 illustrates an embodiment of a scanning device 300 in a closed-door configuration that includes a built-in touchscreen 310 and a built-in imaging device (not shown) to capture images of sample material contained within a chamber (not shown). A user can control the built-in imaging device with the touchscreen 310. In some embodiments, the scanning device 300 is a standalone device that does not require a separate electronic device, remote server, and/or network connectivity to analyze sample tangible objects and determine an attribute of a tangible object. In other embodiments, the scanning device can be part of a system that includes a server configured to process image data that is received over a network from a handheld mobile device or the scanner device itself. For example, a remote server can determine an attribute of a tangible object based on the processed image data and return the results to the scanning device 300 for a user. In some embodiments, the imaging device can contain a microscope/special lens and/or have an optical filter between the imaging device and the sample, or the sample could be disposed under a microscope slide.

Figure 5:
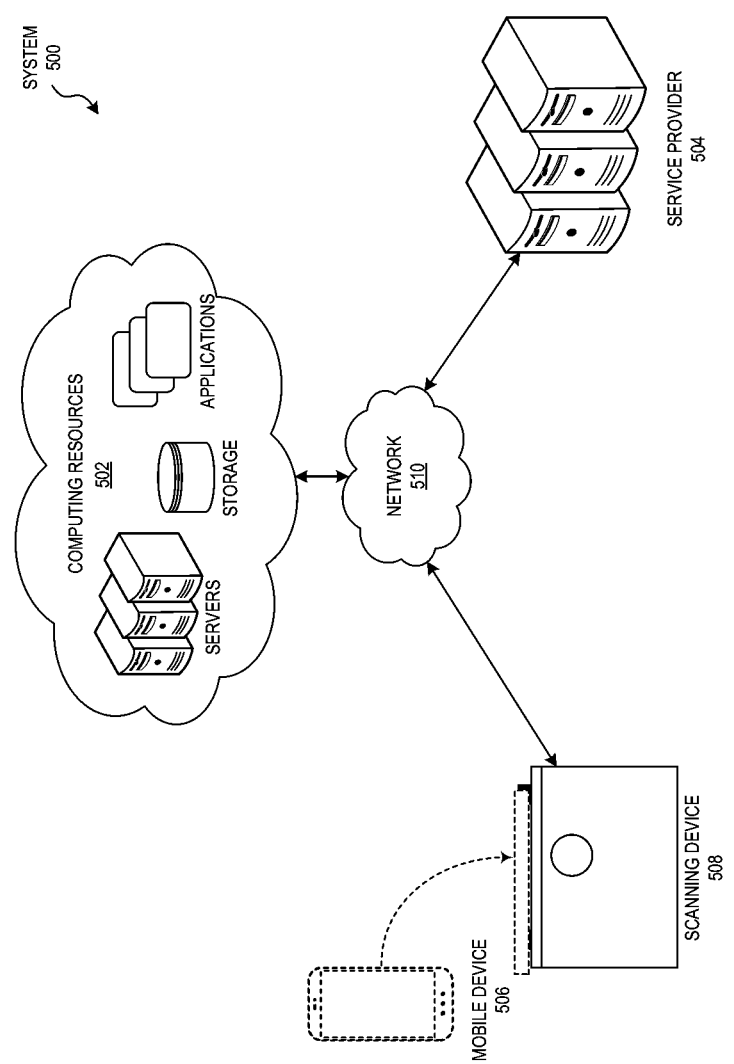
FIG. 5 is a block diagram that illustrates a system operable to ascertain attributes of a tangible object based on image data.

FIG. 5 is a block diagram of a system that can implement at least some aspects of the disclosed technology. The system 500 includes components such as computing resources 502, one or more service provider servers 504 that use the computing resources 502 to ascertain attributes of tangible objects based on image data captured with the scanning device 508 (e.g., scanning devices 100, 200) by, for example the mobile device 506 mounted on the scanning device 508 or captured by a imaging device integrated in the scanning device 508, which are interconnected over a network 510, such as the Internet, to facilitate accurate testing of a tangible object. The network 510 can include a local area network (LAN), a personal area network (PAN), a backbone network, a metropolitan area network (MAN), a wide area network (WAN), enterprise private network, virtual private network (VPN), etc.

The network 510 can include any combination of private, public, wired, or wireless portions. Data communicated over the network 510 may be encrypted or unencrypted at various locations or along different portions of the network 510. Each component of the system 500 may include combinations of hardware and/or software to process data, perform functions, communicate over the network 510, etc. For example, any component of the system 500 may include a processor, memory or storage, a network transceiver, a display, an operating system, and application software (e.g., for providing a user portal), etc. The system 500 can instantiate one or more virtual machines (VMs) that emulate functions or computing resources. Other components, hardware, and/or software included in the system 500 are well known to persons skilled in the art and, as such, are not shown or discussed herein.

The computing resources 502 (e.g., cloud-based, local hosting, offline computing) can provide private computing resources or access to a shared pool of configurable cloud-based computing resources including servers, storage, applications, software platforms, networks, services, etc. The computing resources 502 are accessible by the service provider servers 504 to offer resources to the mobile device 506, which is mountable on the scanning device 508. The service provider servers 504 may include any number of computing devices that provide applications for services that allow users to ascertain the quality and authenticity of plant material. Although shown separate from the computing resources 502, the service provider servers 504 can be part of the computing resources 502.

The computing resources 502 can process image data of tangible objects captured by the mobile device 506 and/or the scanning device 508. For example, the service provider servers 504 can train an ML model and implement that ML model to ascertain the quality and authenticity of tangible objects. The analysis can involve using computer vision (CV) techniques to analyze the physical characteristics of tangible objects captured in images.

CV algorithms can include processes for acquiring, processing, analyzing or understanding digital images, and extraction of high-dimensional data from the real world in order to produce numerical or symbolic information (e.g., in the form of decisions). Understanding in this context means the transformation of visual images (e.g., pictures) into descriptions of the world that make sense to thought processes and elicit appropriate action. This image understanding can be seen as the disentangling of symbolic information from image data using models constructed with the aid of geometry, physics, statistics, and ML.

In some embodiments, attributes of a tangible object can be verified by implementing CV and deep ML algorithms to build an ML model that can be trained from a set of labeled reference images. A database of reference images includes samples of tangible objects that can be used to train the ML model. For example, the database can store images of the same tangible object in two or more attribute categories. The reference images can include images that represent each of the possible or expected attributes. An attribute of a tangible object captured in a sample image can be discovered or verified against the ML model trained on the reference images. The database can also store images of tangible objects verified for attributes that are not expected in sample images of the tangible objects, to create a mismatch or unknown category.

Each of the reference images stored in one or more databases can be labeled with one or more attributes that are identified or verified using an independent method. The attributes can be qualitative or quantitative, or a combination of both. The methods used to verify attributes can include a wide range of methods and processes. Scientific methods for attribute verification can include morphological, microscopic, chemical, and genetic analyses, among others. The methods can also include identification or measurement of specific chemical constituents or mineral compounds, pH, density, weight, and salinity. The attributes of tangible objects can be verified with organoleptic and sensory analysis to examine the taste, aroma, texture, or pattern of materials. Attributes that cannot be directly measured from an image of sample material, such as origin and growing conditions, can be verified by other means such as by reviewing written paper or electronic, verbal, or photographic records. In some cases, an attribute is a product name, container, batch, sample, or lot number.

The sample images of tangible objects that are processed by the ML model can be fed back to train the ML model, thereby improving the ability of the ML model to precisely and/or accurately identify attributes of diverse tangible objects. To further improve the performance of the model, the sample images can undergo one or more secondary processing steps (e.g., pre-processing or post-processing steps).

Examples of secondary processing steps include de-skewing to align an image with a particular axis, despeckling to remove positive or negative spots or to smooth edges, binarization to convert an image from color or greyscale to black-and-white. The task of binarization can be performed as a way of separating certain features from other features of an image or to identify the background of a staging surface, which can enable accurate cropping. Other examples of secondary processing steps include line removal (e.g., clean up non-glyph boxes and lines), layout analysis (e.g., identifying zones), object segmentation (e.g., separating image artifacts or objects), normalizing an aspect ratio, or scaling.

A non-exhaustive list of yet other examples of secondary processing steps of sample image include adding or removing noise (i.e., denoise); adjusting resolution, brightness, color, or contrast; cropping, resizing, rotating, and/or parsing an image into pieces or portions; implementing a bounding box, applying edge enhancements; feature extraction; applying one or more filters (e.g., gaussian blur, convolution, smoothing, greyscale, gradation transformation); flip augmentation; equalization; geometric corrections; histogram equalization; intensity adjustment; intensity windowing; morphology (e.g., smoothing edges); peripheral equalization; text processing; thresholding; or unsharp masking of an image.

In some embodiments, the scanning device can perform an optical character recognition (OCR) process to identify or read words, logos, or barcodes. For example, the scanning device can capture a quick response (QR) code on a box that holds a tangible object. An attribute of the tangible object can be inferred from the QR code on the box. The scanning device can also include a printer to print a QR code based on results (e.g., certificate of analysis (CoA)) or send the QR code to a separate printer. A user can then affix the printed label to the tangible object or a container that holds the tangible object.

The mobile device 506 (or imaging device of the scanning device 508) is operated by a user and interacts with the system 500. An example of the mobile device 506 is a smartphone (e.g., APPLE IPHONE, SAMSUNG GALAXY), or any other handheld mobile device with a camera that is capable of being calibrated for capturing reliable images of samples to enable ascertaining attributes of a captured image of a sample material. The mobile device 506 is also capable of communicatively coupling with the service provider servers 504 over the network 510 via wired (e.g., ethernet) and/or wireless technologies (e.g., Wi-Fi, BLUETOOTH). In some embodiments, any images of sample material captured at the scanning device 508 can be processed locally at the scanning device 508 with local hardware and software that is loaded at the handheld mobile device 506 or some other local computing device. In other words, at least some of the functions performed by the computing resources 502 and/or the service provider 504 can be performed locally at the scanning device 508.

The disclosure is not limited to a smartphone mounted on a separate scanning device. Examples of other suitable handheld mobile devices that can be mounted on the scanning device 508 include laptop computers (e.g., APPLE MACBOOK, LENOVO 440), tablet computers (e.g., APPLE IPAD, SAMSUNG NOTE, MICROSOFT SURFACE), or any other mobile device that has an adequate imaging device and capabilities to communicate over the network 510. In some embodiments, the scanning device 508 is a specialized device that has the components of the mobile device 506 necessary to practice the disclosed embodiments.

In some embodiments, the service provider servers 504 provide or administer a user interface (e.g., website, app) accessible from the mobile device 506. The user interface may include menu items for selecting image capture and/or processing operations and to present analytics about the quality and authenticity of plant material. The user interface may also provide certificates of authenticity that can be shared with interested third-parties.

To provide reliable results regarding attributes of a tangible object, the disclosed embodiments can implement artificial intelligence (AI) techniques based on a broad range of images collected from diverse sources, and images of tangible objects that have been authenticated by other generally accepted techniques such as morphological, chemical, and/or genetic analysis. In one example, the disclosed embodiments implement CV/ML technology as described earlier to ascertain the attributes of tangible objects. Specifically, users can upload images of tangible objects with their mobile phones or other mobile devices to a service that is remotely located from the locations where the images of tangible objects were captured. The users can receive results from the service on their same mobile phones, a tablet computer or on any other computing device or on the scanning device.

The service can be built on top of a unified platform. Hence, the disclosed architecture gives a broad range of customers access to a service by using mobile phones or other devices (e.g., tablet computer, personal computer) and networks that are ubiquitous in even remote parts of the world and may only require access to a relatively inexpensive scanning device to normalize the images of the sample materials for reliable, consistent, and trusted results. For example, the disclosed solution can be deployed with cloud resources to take full advantage of the cloud's flexibility and scalability. The solutions and cloud resource management are both provided via a simple user interface. This allows administrators to allocate resources as needed, and to start/stop servers at a chosen schedule. The combination of unique computer vision technology and scalable platform on the cloud allows for the rapid development of accurate and robust solutions to enhance a process for determining various attributes of tangible objects.

The disclosed CV/ML technology is trained with authenticated images of diverse tangible objects that have been pre-processed according to acceptable commercial practices. The training images can include combinations of materials, impurities, and contaminants for detection in subsequent samples. Hence, the service combines computer vision and deep learning technology on a scalable platform to bring affordable and unique capabilities to users throughout the world. In some embodiments, the disclosed technology implements a variety of image recognition algorithms that combine both image matching with deep learning. This combination allows the algorithms to complement each other in order to maximize performance and accuracy.

In some embodiment, the service defines metadata, which includes characteristics used to detect and identify materials and impurities. In some embodiments, the attribute identification service is continuously trained by capturing training images obtained from various sources and that include tangible objects that has been authenticated in accordance with traditional techniques. The training images can be uploaded by a variety of means to extract features that are labeled and stored as labeled features in a database. Examples of labeled features include species, plant or animal part, or a variety of physical properties such as colors, dimensions, densities, etc. In some examples, objects such as rocks, sticks, and rodent excreta are labeled. In some embodiments, the labeling of images and features in a training set is done automatically with detection methods and/or manually with skilled workers to provide a uniform and consistent assessment of tested material.

In some embodiments, the training of the authentication service involves setting-up training parameters that are continuously adjusted to control an efficiency and accuracy of processing. For example, a training job can be launched periodically based on images of authenticated tangible objects to routinely update and adjust a database. The database could be tested and/or recalibrated for accuracy by periodically submitting images of tangible objects with identified quality and impurities.

As such, the service can detect a range of tangible objects and impurities to suggest relevant labels for recognizable features. A combination of recognizable features detected in an image can be used to identify the attributes of tangible objects. The service can be deployed on a variety of networks including servers that are located in a centralized location or in a decentralized architecture such as a blockchain network that ensures the reliability of results and tracking with sophisticated fault tolerance. In some embodiments, a cluster of servers is configured to run and scale the service as needed. The service could also include a computing interface integration for a variety of applications to further increase the usability of the service.

In some embodiments, the service can implement an artificial intelligence technique that follows vision processing of conventional skilled workers but in a way that ensures uniformity for reliable and accurate results. For example, a convolutional neural network (CNN) could emulate the response of an individual neuron to visual stimuli, where each convolutional neuron processes data for its receptive field. Although fully connected feedforward neural networks can learn features as well as classify data, it is not necessarily practical to apply this architecture to images because a very large number of neurons would be necessary due to the very large input sizes associated with images, where each pixel is a relevant variable. The convolution operation of the CNN solves this problem because it reduces the number of free parameters. For example, regardless of image size, tiling regions of size 5×5, each with the same shared weights, require only 25 learnable parameters. In this way, a CNN can resolve the problems that occur when training traditional neural networks with many layers by using backpropagation. As such, a CNN can reliably find patterns in images to ascertain the attributes of tangible objects.

Figure 6:
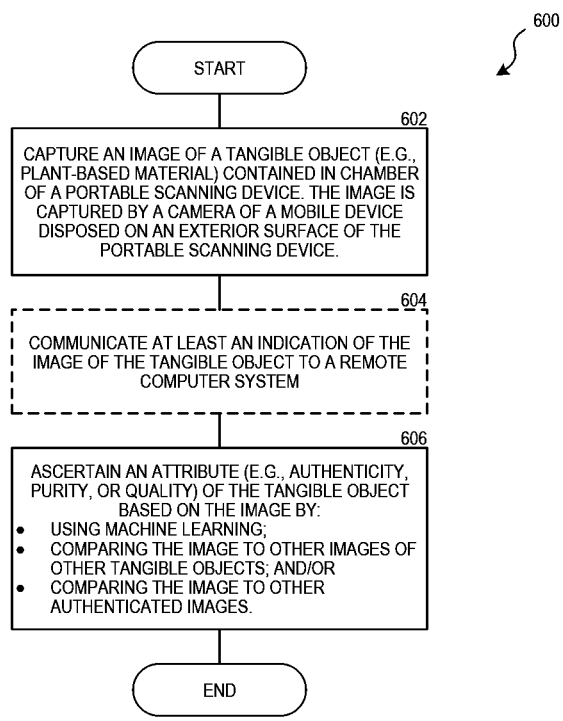
FIG. 6 is a flowchart that illustrates a method performed by a scanning device to ascertain an attribute of a tangible object.

FIG. 6 is a flowchart that illustrates a method performed by a scanning device to ascertain an attribute of a tangible object. In step 602, the handheld mobile device captures an image of a sample of the tangible object contained in an enclosed chamber of a portable scanning device. The image is captured by a camera of a mobile device when disposed on an exterior surface of the portable scanning device. Although the method 600 is described in the context of using a removable handheld mobile device, the method 600 can apply to a scanning device that includes the imaging device and/or some or all the hardware and software components required to perform a determination of an attribute of the tangible object, such as the scanning device of FIG. 3.

In step 604, the handheld mobile device can communicate image data of the captured image to a remote computer system. The remote computer system analyzes the image data to ascertain one or more attributes of the tangible object. The remote computer system then returns results over the network to the handheld mobile device. Although described in the context of a system that involves communications between the handheld mobile device and a remote computer system, the method 600 is applicable to scanning devices that incorporate the hardware and software components required to perform a determination of an attribute of the tangible object. On the other hand, decoupling the scanning device components that process the image data could reduce the expense of the scanning device while increasing the usability with handheld mobiles devices that have different optical and communications capabilities. In other words, the resource intensive processing can be offloaded to the remote server system to provide reliable results while avoiding the need for a cost-prohibitive scanning device.

In step 606, the handheld mobile device itself can ascertain an attribute of a tangible object based on image data. In some embodiments, the tangible object is a plant-based material. The attribute of the plant-based material is ascertained in accordance with machine learning techniques as described elsewhere in this description. In some embodiments, the attribute of the tangible object is ascertained by comparing the captured image to image data of multiple other tangible objects. In some embodiments, the attribute is ascertained by comparing the image data to authenticated images including other images of the same tangible object. In some embodiments, the scanning device can include local resources with reduced capabilities that can be employed when the remote computer system is unavailable. For example, the local resource can provide a rough estimate of an attribute for a user when the remote computer system is unavailable due to a lack of network connectivity. When the network connectivity becomes available, the scanning device can feed the image data to the remote computer system, which can validate the locally obtained results and/or provide information about additional attributes that could only be determine with the computational resources of the remote computer system.

Figure 7:
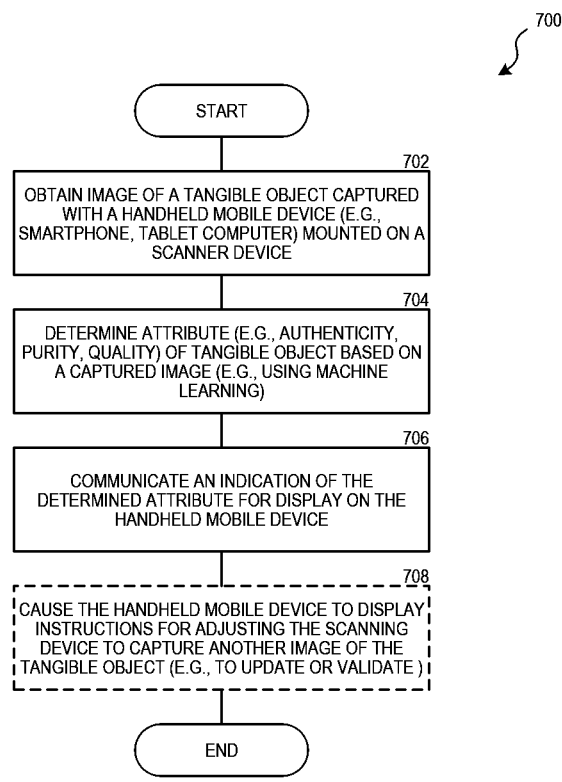
FIG. 7 is a flowchart that illustrates a method performed by a system including a scanning device to ascertain an attribute of a tangible object.

FIG. 7 is a flowchart that illustrates a method performed by a system including a scanning device to ascertain an attribute of a tangible object. In step 702, a service obtains, over a communications network, image data captured with an imagining device (e.g., camera) of a handheld mobile device mounted on a scanning device. In some embodiments, the method is performed at least in part by a private network or cloud-based service that is communicatively coupled to the handheld mobile device over the communications network.

In step 704, the service determines one or more attributes of the tangible object based on a combination of visual features detected in the captured image data of the tangible object. In some embodiments, the tangible object includes a contaminant. In some embodiments, the attributes (e.g., quality, purity, or authenticity) of the plant material is determined in accordance with ML techniques. In some embodiments, determining the quality, purity, or authenticity of the tangible object includes detecting the visual features in the captured image of the tangible object, and identifying contents of the tangible object based on the combination of detected visual features. In some embodiments, the entire image is classified, or some, part, or a portion of the image is classified (e.g., a cropped image). In some embodiments, the system can detect specified objects and can count a quantity of the specified object or determine the area or percent area of the object or objects.

In step 706, the service communicates the ascertained attributes of the tangible object over the communications network to the handheld mobile device. In optional step 708, the service can cause the handheld mobile device to display instructions and/or automatically adjust the camera to capture another image of the tangible object or to adjust and/or validate an ascertained attribute.

As described with respect to the method 600, the method 700 similarly applies to a scanning device that includes some or all of the resources required to identify an attribute of a tangible object such that network connectivity and/or a remote computer system is not required to perform the method 700.

Figure 8A:
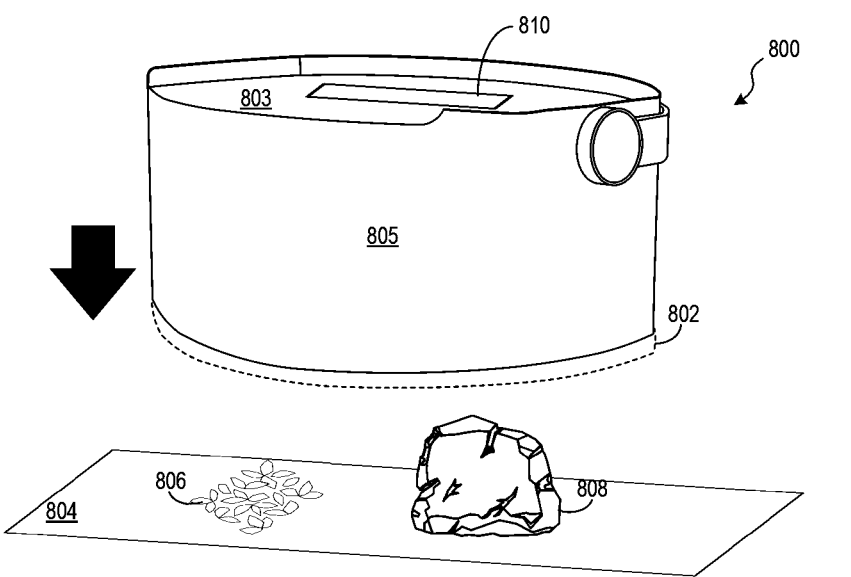
FIG. 8A illustrates an embodiment of a scanning device with a transparent wall or opening positioned over a staging surface on which tangible objects are disposed.
Figure 8B:
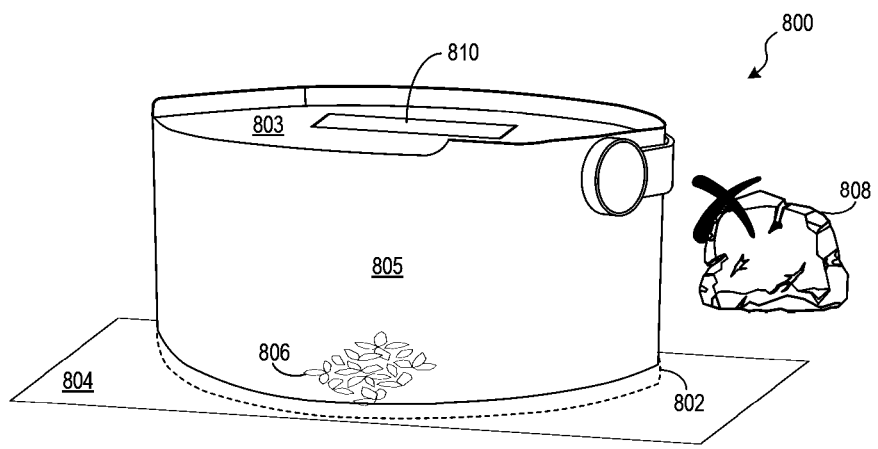
FIG. 8B illustrates an embodiment of a scanning device with a transparent wall or opening positioned on a staging surface on which tangible object is disposed.

FIGS. 8A and 8B illustrate another embodiment of a scanning device 800. Specifically, FIGS. 8A and 8B illustrate a perspective view of the scanning device 800 with a transparent wall or opening positioned over or on a staging surface 804 on which tangible objects are disposed. The embodiments of FIGS. 8A and 8B allows for analyzing tangible objects that are too large (e.g., tree bark on a tree) to sample in a small chamber and/or cannot be removed from something to load in a chamber (e.g., a rash on an arm).

In one example, the scanning device 800 includes the transparent wall 802 such that an imaging device positioned relative to an opaque wall 803 inside of the scanning device 800 can capture images of tangible objects through the transparent wall 802. An opaque body 805 extends from a diameter of the opaque wall 803 to the transparent wall 802. For example, as shown in FIG. 8A, the scanning device 800 is positioned a distance over a staging surface 804 upon which two different types of tangible objects are disposed. A first tangible object includes plant material 806 that lies flat on the staging surface 804 and a second tangible object is a rock 808 that does not lie flat on the staging surface 804. The natural external light can be used to at least partially illuminate tangible objects. Hence, the environment for capturing images of the tangible objects is not fully controlled because external light affects the image data.

The transparent wall 802 can be pressed against the staging surface 804 to create a sealed chamber using the staging surface 804. Hence, the sealed chamber can function like the scanning devices 100 or 200 to create a controlled environment that blocks external light from a captured imaged, thereby controlling the light used to illuminate a tangible object. However, as illustrated with FIG. 8B, creating a chamber by pressing the transparent wall 802 against the staging surface 804 would only function for tangible objects that are relatively flat. For example, the scanning device 800 could be pressed against human tissue to capture an image of a flattened mole. As shown in FIG. 8B, the scanning device 800 could be pressed against the staging surface 804 to capture an image of the plant material 806 but not the rock 808. The opaque body 805 that is pressed against the staging surface 804 can include a flexible material (not shown) such as a rubber seal with an accordion structure that surrounds an exterior of the diameter of the transparent wall 802, which can be pressed against a non-flat surface that is larger than the chamber or over non-flattened samples and still create an environment enclosed from external light.

In another embodiment, the transparent wall 802 is omitted from the scanning device 800 such that the opaque body 805 has an opening to the external environment. The scanning device 800 can create a seal that blocks external light when pressed against the staging surface 804 and accommodate tangible objects with more complex dimensions because the tangible objects would be housed inside the chamber of the scanning device 800. In some embodiments, the scanning device 800 has a flexible seal (not shown) around a diameter of the opening. The seal can be formed of a flexible material (e.g., rubber) and have an accordion structure such that the opaque body 805 can form a seal over a curved staging surface that is larger than the opening to block external light from the chamber.

In yet another embodiment, the transparent wall 802 is removable. As such, different types of transparent walls can be used to create optical filters that enhance the images captured by the imaging device of the scanning device 800. For example, a transparent wall can include a collimating filter or a filter for particular wavelengths to effectively obtain a pre-processed image of a tangible object. Embodiments of a scanning device can omit any number of walls or include any number that can be opened or closed. That is, a scanning device can have multiple openable members to place materials into the chamber from different directions.

The scanning device 800 includes a built-in touchscreen 810 and a built-in imaging device (not shown) to capture images of tangible objects contained within a chamber (not shown). A user can control the built-in imaging device with the touchscreen 810. Similar to scanning device 300, the scanning device 800 is a standalone device that does not require a separate electronic device, remote server, and/or network connectivity to analyze a tangible object and determine an attribute of the tangible object. In other embodiments, the scanning device can be part of a system that includes a remote server system configured to process image data that is received over a network from the scanner device 800.

As illustrated in FIG. 8A, the imaging device of the scanning device 800 can simultaneously capture an image include two or more different types of tangible objects, the plant material 806 and the rock 808. The image processing algorithms of the service can detect the separate tangible objects and crop each of them automatically to analyze the relevant characteristics of respective tangible objects. The scanning device 800 can also automatically crop the image of a tangible object to analyze only a portion of that image, and then extrapolate an attribute for the entire tangible object based on the analyzed tangible object.

In embodiments similar to the scanning devices 100 and 200, a handheld mobile device can be disposed on an exterior surface of the scanning device 800 where a camera lens is positioned to capture images of tangible objects through an opening of the scanning device 800. An opening through the exterior surface to the chamber enables the camera of the handheld mobile device to capture the image of the tangible object in the chamber. The scanning device 800 is illustrated without a door but could optionally include one or more openings that allow external light to enter the chamber, and ultimately illuminate a tangible object. The opening may be covered by transparent panels that allow a user to see samples inside the chamber from the top of the scanning device 800. In one example, the imaging device is a video camera that captures images of tangible objects fully contained in the box or of materials that are moving relative to the scanning device 800. In other words, the scanning device can be moved across a large tangible object, or mounted on a production line with a conveyor belt with the objects moving on them below a camera of the scanning device.

Figure 9:
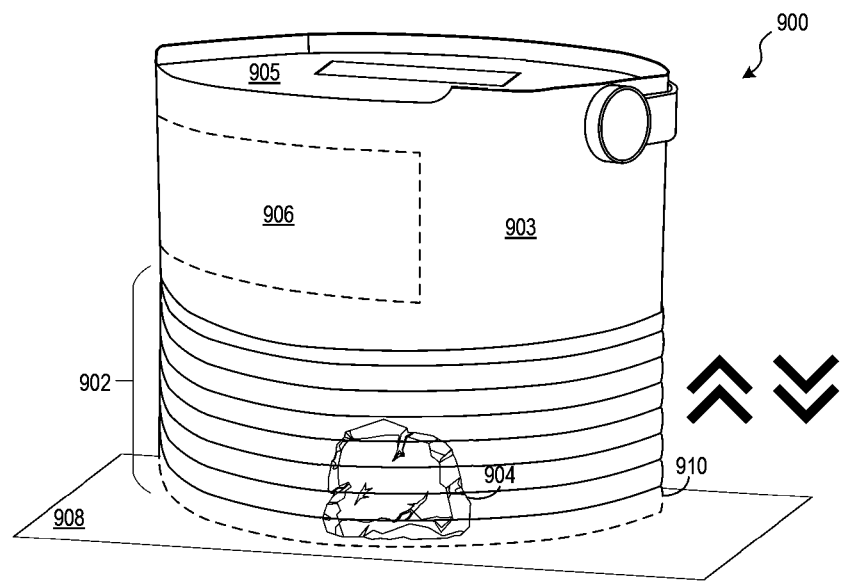
FIG. 9 illustrates a scanning device with an expandable body.

FIG. 9 illustrates another embodiment of a scanning device 900. Specifically, FIG. 9 illustrates a perspective view of the scanning device 900 with an expandable structure 902 of an opaque body 903 that spans the diameter of the scanning device 900. An opaque wall 905 is configured to position an imaging device to capture an image of the tangible object 904 (illustrated as though the opaque body 903 is transparent to aid in understanding). The opaque body 903 extends from a diameter of the opaque wall 905 to a diameter of a staging area. The expandable structure 902 is illustrated with accordion-like bellows that are collapsible and expandable to change the size of the internal chamber of the scanning device 900. Although depicted with bellows, the expandable structure 902 can be formed of any expandable material or structure such as an opaque fabric curtain that blocks external light from the internal chamber.

In some embodiments, the scanning device 900 includes an openable member 906 similar to the scanning devices 100, 200, or 300. Rather than including shelves for setting a tray at different distances from an imaging device, a tangible object is disposed on a bottom wall 910 of the scanning device 900 and the expandable structure 902 is expanded or collapsed to adjust the focal distance to the tangible object. In another embodiment, the scanning device 900 omits the bottom wall 910 similar to an embodiment of the scanning device 800. As such, the scanning device 900 can form a sealed chamber by being pressed against a staging surface 908. However, unlike the scanning device 800, the expandable structure 902 can be expanded or collapsed to change the focal distance from the imaging device to the tangible object 904 while maintaining the chamber sealed from exterior light. Moreover, an embodiment of the scanning device 800 without the bottom wall 910 obviates the need for the openable member 906. Thus, the exterior of the scanning device 900 and chamber could be of any color and material that blocks light, and could be firm or flexible, such as the case of something that can collapse like an accordion or fold-up like a pop-up tent.

Although illustrated with an expandable structure 902 that expands/contracts vertically, embodiments of the scanning device can be expandable horizontally and/or vertically to accept bulky objects. The scanning device can include accordion-like folding sides and/or sliding or telescoping walls. The housing or chamber of the scanning device can be made of a variety of material types, both rigid and flexible (e.g., plastic, wood, metal, cardboard, paper, fabric, rubber, nylon). The housing or chamber can be made of rigid internal or external poles/skeleton holding a rigid or flexible material that could be folded/collapsed. The housing or chamber can have sides that are not perpendicular to the base/bottom (e.g., angled so the scanning device is wider at the base compared to the top. The chamber can have a camera on a side alone, multiple cameras either on one side/top or multiple sides. The camera or lights do not have to be on opposite sides of the chamber as the shelf/object holding the tangible object. For example, a side-mounted camera can capture a profile image of a tangible object. The scanning devices can include connectors to connect to equipment or surfaces (e.g., clamps, clips, hooks), wheels on the bottom, etc.

Thus, the shape of the housing for a scanning device is not limited to any particular external geometries so long as the internal dimensions (e.g., height, depth, width) form a chamber that can stage tangible objects for an imaging device to capture images that can be processed to determine attributes of the tangible objects. Moreover, a staging area must provide a minimum distance from the opening or imaging device to allow the imaging device to focus on the tangible objects. However, there is no restriction for a maximum focal distance from the imaging device. In some instances, the tangible objects are treated in some way before images are captured inside the chamber. For example, the tangible object can be treated by adding a substance such as a dye, water, or a chemical.

Although embodiments described herein mainly include a portable scanning device, the disclosed technology can be implemented in non-portable devices. For example, the scanning devices can be implemented as kiosk-type devices located in a factory, or at neighborhood buildings, retail stores, etc.

Figure 10:
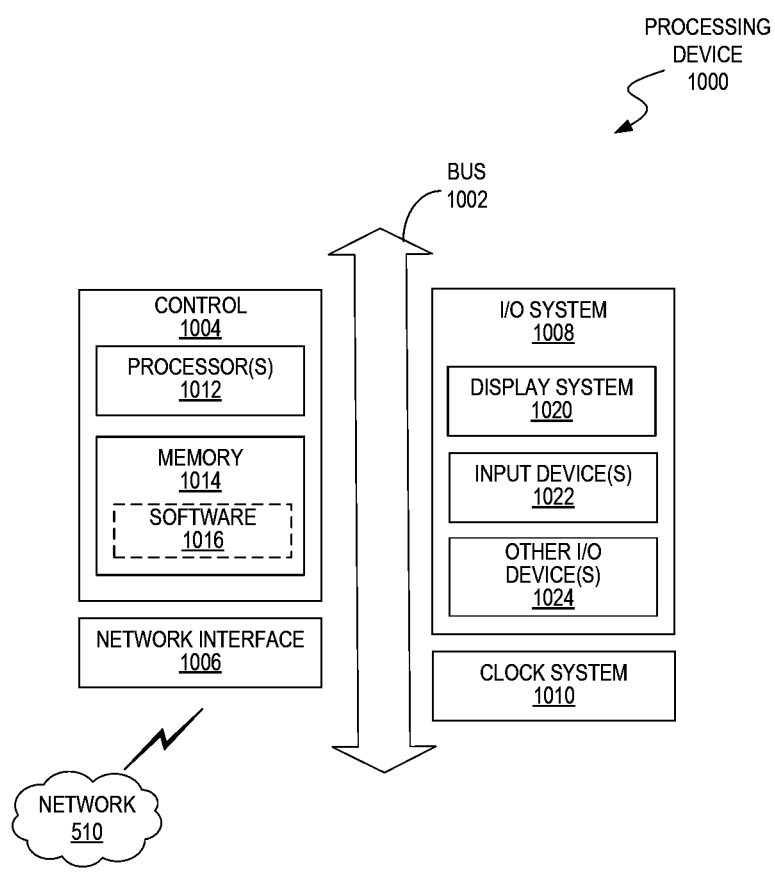
FIG. 10 is a block diagram that illustrates a processing device operable to implement at least some aspects of the disclosed technology.

FIG. 10 is a block diagram that illustrates a processing device 1000 (e.g., scanning device or service server) operable to implement the disclosed technology. As shown, the processing device 1000 includes a bus 1002 that is operable to transfer data between hardware and/or software components. These components include a control 1004 (e.g., processing system), a network interface 1006, an input/output (I/O) system 1008, and a clock system 1010. The processing device 1000 may include other components that are not shown nor further discussed for the sake of brevity. One of ordinary skill in the art will understand any hardware and software that is included but not shown in FIG. 10.

The control 1004 includes one or more processors 1012 (e.g., central processing units (CPUs)), application-specific integrated circuits (ASICs), and/or field-programmable gate arrays (FPGAs), and memory 1014 (which may include software 1016). For example, the memory 1014 may include volatile memory, such as random-access memory (RAM) and/or non-volatile memory, such as read-only memory (ROM). The memory 1014 can be local, remote, or distributed.

A software program (e.g., software 1016), when referred to as "implemented in a computer-readable storage medium," includes computer-readable instructions stored in the memory (e.g., memory 1014). A processor (e.g., processors 1012) is "configured to execute a software program" when at least one value associated with the software program is stored in a register that is readable by the processor. In some embodiments, routines executed to implement the disclosed embodiments may be implemented as part of operating system (OS) software (e.g., MICROSOFT WINDOWS, LINUX) or a specific software application, component, program, object, module, or sequence of instructions referred to as "computer programs."

As such, computer programs typically comprise one or more instructions set at various times in various memory devices of a computer (e.g., processing device 1000), which, when read and executed by at least one processor (e.g., processor 1012), will cause the computer to perform operations to execute features involving the various aspects of the disclosed embodiments. In some embodiments, a carrier containing the aforementioned computer program product is provided. The carrier is one of an electronic signal, an optical signal, a radio signal, or a non-transitory computer-readable storage medium (e.g., memory 1014).

The network interface 1006 may include a modem or other interfaces (not shown) for coupling the processing device 1000 to other computers over the network 510. The I/O system 1008 may operate to control various I/O devices, including peripheral devices such as a display system 1020 (e.g., a monitor or touch-sensitive display) and one or more input devices 1022 (e.g., a keyboard and/or pointing device). Other I/O devices 1024 may include, for example, a disk drive, printer, scanning device, or the like. Lastly, the clock system 1010 controls a timer for use by the disclosed embodiments.

Operation of a memory device (e.g., memory 1014), such as a change in state from a binary one (1) to a binary zero (0) (or vice versa) may comprise a visually perceptible physical change or transformation. The transformation may comprise a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

While embodiments have been described in the context of fully functioning computers, those skilled in the art will appreciate that the various embodiments are capable of being distributed as a program product in a variety of forms and that the disclosure applies equally, regardless of the particular type of machine or computer-readable media used to actually effect the embodiments.

While the disclosure has been described in terms of several embodiments, those skilled in the art will recognize that the disclosure is not limited to the embodiments described herein and can be practiced with modifications and alterations within the spirit and scope of the invention. Those skilled in the art will also recognize improvements to the embodiments of the present disclosure. All such improvements are considered within the scope of the concepts disclosed herein. Thus, the description is to be regarded as illustrative instead of limiting.

We claim:

1. A scanning device comprising:
   a housing including:
      an opaque wall configured to position an imaging device to capture an image of a tangible object;
      a transparent wall opposite of the opaque wall;
      an opaque body extending from a diameter of the opaque wall to the transparent wall; and
      a chamber configured to enable the imaging device to capture the image from inside the chamber through the transparent wall,
         wherein a focal distance from the imaging device to the transparent wall enables capturing a physical characteristic of the tangible object in the image at a resolution that enables ascertaining an attribute of the tangible object, and
         wherein the physical characteristic of the tangible object includes a color, size, shape, texture, or pattern.

2. The scanning device of claim 1, wherein the opaque body includes an expandable structure configured to:
   increase the focal distance between the imaging device and the transparent wall by extending the expandable structure; and
   decrease the focal distance between the imaging device and the transparent wall by collapsing the expandable structure.

3. The scanning device of claim 2, wherein the expandable body comprises:
   a plurality of baffles to change a length of the expandable body.

4. The scanning device of claim 1, wherein the opaque body includes an expandable structure to increase a dimension of the opaque body to contain a tangible object larger than a smallest volume of the chamber.

5. The scanning device of claim 1, wherein the attribute of the tangible object includes an authenticity, purity, or quality.

6. The scanning device of claim 1, wherein the imaging device is integrated in the scanning device.

7. The scanning device of claim 1, wherein a distance from the imaging device to a staging area on which the tangible object is disposed is greater than the focal distance when the image is captured such that an external light illuminates the tangible object.

8. The scanning device of claim 1 further comprising:
   a light source configured to illuminate a staging area through the transparent wall,
      wherein the tangible object is disposed on the staging area.

9. The scanning device of claim 1, wherein the transparent wall is removable and includes a light filter such that the image is filtered by the light filter.

10. The scanning device of claim 1, wherein the scanning device creates a controlled environment that blocks out external light when the transparent wall is sealed against a staging area and the tangible object is disposed between the transparent wall and the staging area.

11. The scanning device of claim 1, wherein the scanning device has an opening or a transparent wall in an area perpendicular to the opaque wall configured for external light to enter the chamber.

12. A scanning device comprising:
   a partially enclosed housing including:
      an opaque wall configured to position an imaging device to capture an image of a tangible object;
      an opening opposite of the opaque wall;
      an opaque body extending from a diameter of the opaque wall to the opening; and
      a partially enclosed chamber configured to enable the imaging device to capture the image from inside the chamber through the opening,
         wherein a focal distance from the imaging device to the opening enables capturing a physical characteristic of the tangible object in the image at a resolution that enables ascertaining an attribute of the tangible object, and
         wherein the physical characteristic of the tangible object includes a color, size, shape, or texture.

13. The scanning device of claim 12, wherein the opaque body includes an expandable structure configured to:
   increase the focal distance between the imaging device and the opening by extending the expandable structure; and
   decrease the focal distance between the imaging device and the opening by collapsing the expandable structure.

14. The scanning device of claim 12, wherein the expandable body comprises:
   a plurality of baffles to change a length of the expandable body.

15. The scanning device of claim 12, wherein the scanning device creates a controlled environment that blocks out external light when sealed against a staging area on which the tangible object is disposed.

16. The scanning device of claim 12, wherein the attribute of the tangible object includes an authenticity, purity, or quality.

17. The scanning device of claim 12, wherein the imaging device is integrated in the scanning device.

18. The scanning device of claim 12, wherein a handheld mobile device includes the imaging device, the scanning device comprising:
   another opening through which the imaging device can capture the image when the handheld mobile device is disposed on an exterior surface of the opaque wall.

19. The scanning device of claim 12, wherein the imaging device includes a video camera for capturing movement relative to the tangible object.

20. A scanning device comprising:
   a housing including:
      an opaque wall configured to position an imaging device to capture an image of a tangible object;
      a staging area opposite of the opaque wall;
      an opaque body extending from a diameter of the opaque wall to a diameter of the staging area and including an expandable structure configured to expand and retract the opaque body between the opaque wall and the staging area; and
      a chamber configured to enable the imaging device to capture the image from inside the chamber toward the staging area,
         wherein a focal distance from the imaging device to the staging area enables capturing a physical characteristic of the tangible object in the image at a resolution that enables ascertaining an attribute of the tangible object, and wherein the physical characteristic of the tangible object includes a color, size, shape, texture, or pattern.

21. The scanning device of claim 20, wherein the expandable body comprises:
a plurality of baffles to change a length of the opaque body.

22. The scanning device of claim 20, wherein the staging area includes a transparent wall configured for the imaging device to capture the image of the tangible object through the transparent wall.

23. The scanning device of claim 20, wherein the staging area is an opening configured for the imaging device to capture the image of the tangible object on a surface separate from the scanning device.

24. The scanning device of claim 20 comprising:
a processor; and
a memory storing instructions that, when executed by the processor, cause the scanning device to:
detect the physical characteristic in the image; and
determine the attribute of the tangible object based on the physical characteristic in the image processed through a machine learning model,
wherein the machine learning model is trained based on a plurality of physical characteristics of a plurality of tangible objects.

25. The scanning device of claim 20 comprising:
a transceiver;
a processor; and
a memory storing instructions that, when executed by the processor, cause the scanning device to:
cause the transceiver to communicate, over a wireless network, image data of the image to a server computer, wherein the physical characteristic is detected at the server computer; and
cause the transceiver to receive, over the wireless network, an indication of the attribute of the tangible object.

* * * * *